United States Patent [19]
Armstrong

[11] Patent Number: 5,607,455
[45] Date of Patent: Mar. 4, 1997

[54] METHOD AND APPARATUS FOR AUTOMATIC SHOCK ELECTRODE ENABLING

[75] Inventor: Randolph K. Armstrong, Missouri City, Tex.

[73] Assignee: Intermedics, Inc., Houston, Tex.

[21] Appl. No.: 450,105

[22] Filed: May 25, 1995

[51] Int. Cl.⁶ .................................................. A61N 1/368
[52] U.S. Cl. .................................................................. 607/8
[58] Field of Search .................................. 607/4, 5, 6, 7, 607/8, 9

[56] References Cited

U.S. PATENT DOCUMENTS

| | | |
|---|---|---|
| 4,140,131 | 2/1979 | Dutcher et al. . |
| 4,800,883 | 1/1989 | Winstrom . |
| 4,964,407 | 10/1990 | Baker et al. . |
| 5,003,975 | 4/1991 | Hafelfinger et al. . |
| 5,383,908 | 1/1995 | Sweeney et al. ............................ 607/5 |

OTHER PUBLICATIONS

Haddad, L., et al., "Troubleshooting Implantable Cardioverter Defibrillator System Malfunctions: The Role of Impedance Measurements," in *Pace*, vol. 17, pp. 1456–1461 (Sep. 1994).

*Primary Examiner*—William E. Kamm
*Assistant Examiner*—Scott M. Getzow
*Attorney, Agent, or Firm*—C. Steven McDaniel; Conley, Rose & Tayon, P.C

[57] ABSTRACT

Methods, circuits and devices useful for maximizing the likelihood of successful defibrillation or cardioversion using an automatic implantable cardioverter/defibrillator ("AICD") system are provided which are capable of monitoring the impedance of AICDs for purposes of detecting lead malfunctions. After detection of a lead malfunction, the methods, circuits and devices are capable of connecting or disconnecting leads and electrodes to maximize the likelihood of effective cardioversion and defibrillation.

27 Claims, 5 Drawing Sheets

METHOD AND APPARATUS FOR AUTOMATIC SHOCK ELECTRODE ENABLING

BACKGROUND OF THE INVENTION

A. Field of the Invention

The present invention relates to a method and apparatus for assuring that an automatic implantable cardioverter/defibrillator ("AICD") provides the necessary shock energy through a preselected combination of electrodes.

B. Description of the Related Art

AICDs deliver shock energy through a combination of electrodes. For example, AICD housings (cans) have been developed which allow an external programmer to enable or disable these electrodes. At implant, the physician may select a combination of electrodes which produces the lowest defibrillation threshold (DFT) or which is the most expedient and least traumatic to the patient. If after implant, one of the electrodes breaks, dislodges or shows a rise in impedance, the likelihood of successful defibrillation or cardioversion procedure may decrease significantly.

In prior art approaches, in order to restore the likelihood of defibrillation or cardioversion, the physician had to diagnose the electrode impedance problem and either implant a new electrode or externally reprogram the AICD to use the remaining functional electrodes. The delay between onset of the impedance problem and the corrective action posed a severe hazard to the patient if arrhythmias occurred during this period.

Lead related problems are not uncommon in AICDs. See, Magney et al., *PACE* 16:445–457 (1993). These failures may arise due to anatomical mechanisms such as failure of central venous catheters adjacent to the sterno-clavicular joint. Problems with AICD leads, such as lead fracture or loose connections, may result in sudden death if ventricular arrhythmias are not detected or not terminated by the AICD. See, Feldman et al., "Identification of An Implantable Defibrillator Lead Fracture With a New Holter System," *PACE* 16:1342–1344 (1993).

In one study, one hundred and fourteen patients undergoing successful implantation of an AICD were monitored. See, "Lead-Related Morbidity in Patients With Cardioverder-Defibrillators Utilizing Non-Thoracotomy Lead Systems," Nallamothu, N. et al., *PACE* Vol. 17 No. 4, Part 2, page 761 (NASPE 1994 Abstracts). Twenty-two patients (19%) experienced after implantation lead-associated events which led to re-operation, re-hospitalization, and/or prolongation of implant hospital stay for alteration of anti-arrhythmic drug therapy. The causation of the lead associated events which led to the alternative therapies included lead dislodgement, lead fracture/malfunction, unacceptable DFT in the followup, and subclavian thrombosis. The study proposed that the calculated incident of failure might be an underestimate, as some devices do not yield information on the lead integrity in routine followup and it is not routine to repeat defibrillation efficacy testing on a long term basis. See also, Troop, P. J., "Implantable Cardioverters and Defibrillators," In Current Problems in Cardiology. Yearbook Medical Publishers, pp. 673–815 (1989).

It is known that monitoring impedance of AICD systems is one means for detecting lead failures. See, "Troubleshooting Implantable Cardioverter Defibrillator System Malfunctions: The Role of Impedance Measurements," Haddad, L. et at., *PACE Vol.* 17 1456–1461 (1994). This study found that external high impedance measurements may be used to troubleshoot AICD system malfunctions due to: lead fractures, faulty adapter connections, and loose set screw connections. However, prior art approaches such as the ones suggested by this study require relatively immediate re-operation to replace the damaged lead.

Routine posterior-anterior and lateral chest x-rays can identify lead fractures prior to any clinical observation. However, other of the cases demonstrate that not all lead or connector problems can be detected by routine chest x-rays.

Certain implantable pacing devices possess a mechanism for switching from a bipolar lead configuration to a unipolar lead configuration when a fault is detected in the bipolar lead ring. See, U.S. Pat. No. 4,964,407. In certain of these devices, a series of high impedance test signals are actively generated (not merely sensed) by a microprocessor in a pacemaker to determine whether a bipolar or unipolar lead is attached. If no operational bipolar lead is detected, the programming of the pacemaker is altered to a unipolar pacing mode. However, similar systems are not available for AICDs.

Methods, circuits and devices are needed which are capable of monitoring the impedance of AICDs for purposes of detecting lead malfunctions. Such systems will avoid the difficulties associated with prior art approaches which require frequent x-raying, inefficient discovery of lead malfunctions using x-raying, or other external monitoring devices. Methods, circuits and devices are also needed which, after detection of a lead malfunction, are capable of connecting or disconnecting leads and electrodes to maximize the likelihood of effective cardioversion and defibrillation. Preferably, such systems will be fully implantable and will not require immediate invasive surgical techniques or frequent x-irradiation in order to correct the problems.

SUMMARY OF THE INVENTION

Systems and methods useful for maximizing the likelihood of successful defibrillation or cardioversion using an automatic implantable cardioverter/defibrillator system are provided by the present invention. The system is capable of monitoring the impedance of AICDs for purposes of detecting lead malfunctions. After detection of a lead malfunction, the system of the present invention is capable of connecting or disconnecting leads and electrodes to maximize the likelihood of effective cardioversion and defibrillation. These systems are fully implantable and do not require immediate invasive surgical techniques or frequent x-irradiation.

Various methodologies may be used to implement the present invention. If a method is desired which can simply connect an electrode in response to a too-high impedance measurement, then the impedance of the AICD system is measured initially. This may occur, for example, during a first shock phase. The measured impedance then is compared to a high impedance threshold value. If the measured impedance exceeds the threshold value, then at least one electrode is electrically connected to the system prior to the next shocking cycle.

Likewise, if a method is desired which can simply electrically disconnect an electrode in response to a too-low impedance measurement, then the impedance of the AICD system is initially measured, for example, during a first shock phase. The measured impedance is then compared to a low impedance threshold. Where the measured impedance drops below the lower threshold, at least one electrode is electrically disconnected from the system, as for example prior to the next shocking cycle.

A combined method for maximizing likelihood of successful defibrillation or cardioversion using an automatic implantable cardioverter/defibrillator system, will be preferred in certain instances. Such a method will comprise a two-stage impedance comparison.

First, an impedance measurement of the system, as for example resulting from a first shock is taken. This value is compared to a high impedance threshold. Where the comparison demonstrates that the impedance measurement is above the upper threshold, one or more electrode is activated into the grid, as for example prior to the next shock. If this occurs, then the method calls for making a second impedance comparison of the system.

If the impedance measurement is below the upper impedance threshold, then the method calls for comparing that impedance measurement to the lower impedance threshold. Where the impedance measurement is below the lower impedance threshold, one or more electrodes are disconnected from the system grid, as for example prior to the next shock in the cycle.

If the impedance measurement is neither above the upper limit nor below the lower limit, the method simply allows the next shock to occur and repeats itself. In this manner, the two-stage method constantly monitors and adjusts for discrepancies in the system impedance.

There are a number of reasons why an AICD system will exhibit impedance discrepancies above or below pre-set thresholds. Among them are lead dislodgement and lead malfunction. Lead dislodgement may occur where the lead shifts due to loss of anchoring in the tissue. In some instances, the dislodgement is temporary and the lead will subsequently return to a position capable of generating the proper impedance. In other cases, the dislodgement is permanent. Other lead malfunctions include lead fracture, or loose set screws at the point of attachment of the electrode tip to the lead. It is also common immediately post-transplantation of an AICD to detect impedance discrepancies due to acute phase tissue stabilization. This is a temporary condition which usually corrects itself with passage of time and infiltration of tissue into the lead and tip.

The methods of the invention may be used with electrodes implanted in a variety of locations surrounding the heart. Typically, such an electrode will include one implanted in or near the superior vena cava or one implanted in or near the patient's coronary sinus. Another typical location for an electrode is in or near the right ventricle. Auxiliary electrodes may also be present such as those which are implanted subcutaneously.

In many modern AICDs, another electrode available for selection with the methods of the invention is the implantable cardioverter/defibrillator can itself. These are typically referred to as "hot" cans. Such can electrodes are routinely implanted pectorally. However, they may also be implanted abdominally.

Thus, the methods of the invention monitor shock electrode impedance after each defibrillation or cardioversion shock. If the impedance exceeds a preset threshold, this invention will enable a preset combination of electrodes to be included in the subsequent shocks in an attempt to reduce the shock electrode impedance. This will provide increased safety for the patient in the case of shock electrode malfunction. For example, a physician may implant an RV-to-SVC+can system but choose to disable the can electrode due to patient discomfort during low energy cardioversion shock. If at a later time, the SVC lead were to break, in one embodiment of this invention, it would be possible to detect the increase in impedance and include the can electrode in all subsequent shocks.

One method of calculating the impedance is by using the formula:

$$R = \frac{t}{C \ln\left(\frac{V_i}{V_f}\right)}$$

where R=impedance; t=duration of delivered shock; $V_i$=pre-shock voltage reading; $V_f$=post-shock voltage reading; and C=capacitance.

Using this formula, an initial reading ($V_i$) is taken at the high voltage capacitor of the AICD just prior to delivery of the high voltage shock (typically 600 or more volts). After the delivery of a shock of duration (t) typically of approximately 10 milliseconds, a second reading ($V_f$) is taken at the same capacitor. The capacitance (C) of the high voltage capacitor is a constant for each such device. The impedance (R) is then calculated by taking the natural log of the ratio of the initial voltage reading to the final voltage reading, multiplying the result by the capacitance constant for the device, and dividing the result into the value for the duration of the delivered shock. While this is a means of measuring and calculating the system impedance found by the inventor to be applicable to many types of AICD systems, it is but one such method. Other methods for measuring and calculating system impedance will be known to those of skill in the art and will work equally well.

The methods of the invention may measure impedance at a capacitor prior to shock and following shock. It a preferred mode, the measurement of impedance will be accomplished at the high voltage (HV) capacitor of the AICD. Again, while this position is one for measuring and calculating the system impedance found by the inventor to be applicable to many types of AICD systems, other positions for measuring and calculating system impedance will be known to those of skill in the art and will work equally well.

The impedance thresholds, both high and low are a function of both the particular AICD system and the particular tissue environment. Thus, each patient's impedance thresholds will be unique to at least some degree. This is especially true where immediately post-implantation, acute phase tissue responses alter the system impedance for at least some time. However, it is possible to approximate certain high impedance thresholds to generally lie approximately between 50 and 100 Ohms. In other embodiments, the high impedance threshold will be approximately between 60 and 80 Ohms. In a preferred mode of practicing the methods of the invention, the high impedance threshold will be approximately 70 Ohms. Thus, for example using the preferred mode, should the measured impedance exceed 70 Ohms, at least one electrode, for instance a hot can electrode will be switched on in order to lower the impedance to a level at or below 70 Ohms.

Similarly, it is possible to approximate certain low impedance thresholds to generally lie approximately between 20 and 60 Ohms. In other embodiments, the low impedance threshold will be approximately between 30 and 40 Ohms. In a preferred mode of practicing the methods of the invention, the low impedance threshold will be approximately 40 Ohms. Again for example using the preferred mode, should the measured impedance fall below 40 Ohms, the additional electrode added to bring the impedance to a level under the high impedance threshold, for instance the hot can electrode, will be switched off in order to raise the impedance to a level at or above 40 Ohms. Other electrode, can be switched off in lieu of the newly connected electrode, as well.

The methods of the invention are utilized with an AICD system which may take a number of configurations. In one of the most common, the system will comprise a hot can electrode, a superior vena cava (SVC) implanted electrode, and a right ventricle (RV) implanted electrode. As initially implanted, the system may have all three electrodes activated (switched on). In this instance, the methods of the invention will monitor for too low impedance and, as necessary, switch one or more electrodes out of the system (typically, either the hot can or the SVC). Alternatively, the physician may activate only the SVC and RV electrodes, leaving the can electrode as an optional electrode to switch on or off as needed using the methods of the invention.

Other configurations of the system are also possible. The system may comprise a hot can electrode, a superior vena cava implanted electrode, a right ventricle implanted electrode, and a subcutaneously implanted electrode. Or, the system may comprise only a hot can electrode, a right ventricle implanted electrode, and a subcutaneously implanted electrode.

The position of implantation of the electrodes of the invention is at the studied discretion of the surgeon. Thus, the methods of the invention will work equally well where the can electrode is implanted pectorally or where it is implanted abdominally. Similarly, the superiorly placed electrode may be implanted in the superior vena cava or equally as well in the coronary sinus. The implantation of the subcutaneous electrode or patch can be in any number of positions so long as the proper circuits can be established.

The invention also provides for circuits useful in maximizing the likelihood of successful defibrillation or cardioversion from an automatic implantable cardioverter/defibrillator system. In parallel to the methods taught by the invention, the circuits of the invention may be circuits for simply switching on a preselected electrode, or for simply switching off a preselected electrode.

Alternatively, the circuits of the invention may combine the capacity to both switch on and to switch off preselected electrodes. In each such circuit, means for measuring the impedance of the system as a result of a first shock emanating from the AICD are required. As described generally above, these means may take the form of a measurement of the pre-shock and post-shock impedance at the high voltage capacitor of the AICD. Where it is desired to monitor and adjust for too high impedance, means for comparing the measured impedance to a high impedance threshold are required.

In those instances where too high an impedance is found (when compared to the high impedance threshold), the circuits of the invention will provide means for connecting at least one electrode to the system prior to the next shock to emanate from the AICD. Where low impedance is of particular concern, the circuits of the invention will provide means for comparing the measured impedance to a low impedance threshold, and means for disconnecting at least one electrode from the system prior to the next shock, when that impedance is approximately below the low impedance threshold. Combined systems will have all means recited above in order to both connect or disconnect the preselected electrode or electrodes as necessary when levels fall above or below the impedance thresholds.

The particular methods and circuits found by the inventor to provide the advantages of the invention will be described in more detail by reference to the following figures and detailed descriptions of the preferred embodiments.

BRIEF DESCRIPTION OF THE DRAWINGS

FIG. 2. A. Heart assisted by a pectoral AICD with electrodes activated in the right ventricle and the superior vena cava. B. Heart assisted by a pectoral AICD with electrodes activated in the right ventricle, the superior vena cava, and subcutaneously. C. Heart assisted by a pectoral AICD with electrodes activated in the right ventricle and subcutaneously. D. Heart assisted by a pectoral AICD with electrodes activated in the right ventricle, the superior vena cava, and at the can. E. Heart assisted by a pectoral AICD with electrodes activated in the right ventricle, the superior vena cava, subcutaneously, and at the can. F. Heart assisted by a pectoral AICD with electrodes activated in the right ventricle, subcutaneously, and at the can. G. Heart assisted by a pectoral AICD with electrodes activated in the right ventricle and at the can. H. Heart assisted by an abdominal AICD with electrodes activated in the right ventricle and the superior vena cava. I. Heart assisted by an abdominal AICD with electrodes activated at the can and the superior vena cava.

DESCRIPTION OF PREFERRED EMBODIMENTS

Figure 1:
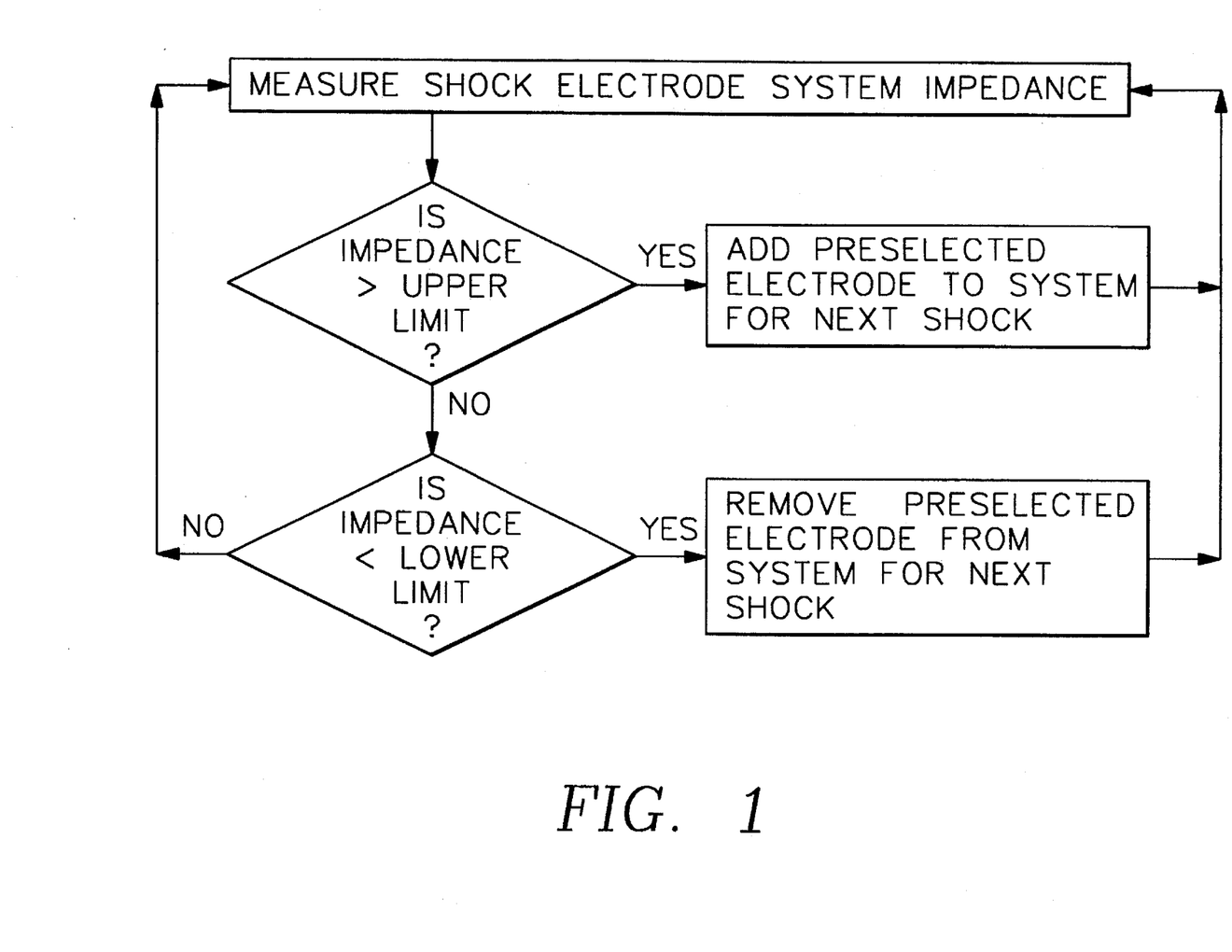
FIG. 1. Shows an operational flow chart illustrating a method of measuring impedance and selecting electrodes.

Referring now to FIG. 1, the general method of the invention is demonstrated in a flow diagram of the decision process. The method depicted is that for a combined process of comparing both high and low impedance thresholds. However, each decision junction along with resulting actions may easily be segregated into single decision loops.

In each such method, the impedance of the shock electrode system is measured as previously described. Once that value has been determined, it is compared to an upper limit or high impedance threshold valve. If the measured impedance is above the upper limit, a preselected electrode is electrically connected to the system and is used to establish the shock field for the next shock. In association with that next shock, the system impedance is again measured. If the measured impedance is not greater than the upper limit, the method calls for a second decision. This decision is accomplished by comparing the measured impedance to a lower limit or low impedance threshold valve. If the measured impedance is below the lower limit, the electrode that was previously added to the system in order to compensate for too high of an impedance (or some other pre-selected electrode), is electrically removed or disconnected from the system. Where the electrode is removed prior to the next shock, the method calls for another measurement of system impedance. Where it is not necessary to add or remove an electrode by virtue of system impedance falling within the acceptable range both high and low, the method of the invention awaits the next shock and repeats the decision-making matrix in continuum.

Referring generally to FIG. 2 A–I, it can be seen that a variety of configurations may be used with the methods and systems of the invention. While these configurations are those most typically encountered in implantable automatic cardioverter/defibrillators, other configurations, other types of electrodes, and other electrode implantation sites may be used similarly in conjunction with the methods and circuits of the invention.

Figure 2A:
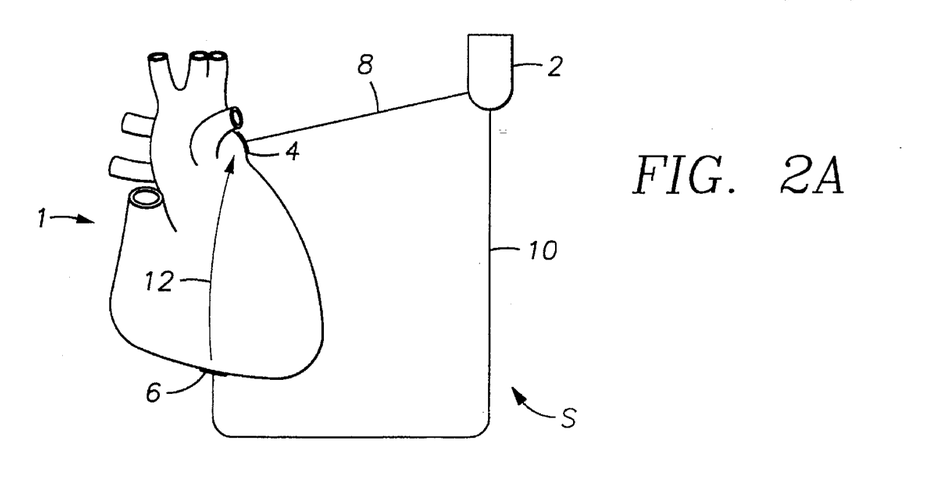
Figure 2B:
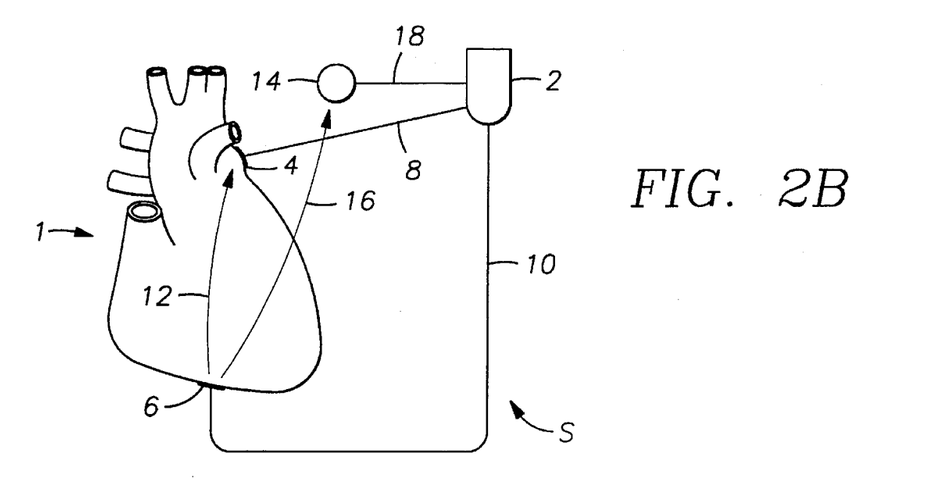
Figure 2C:
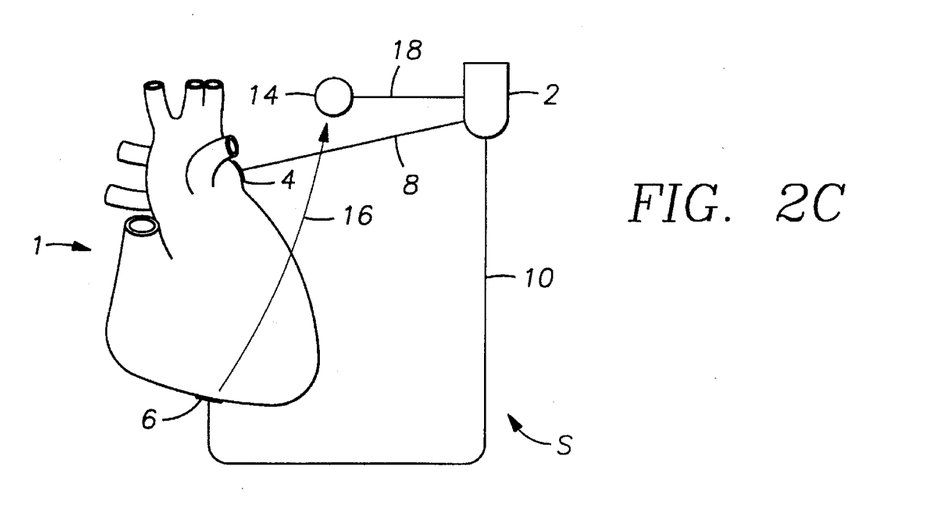
Figure 2D:
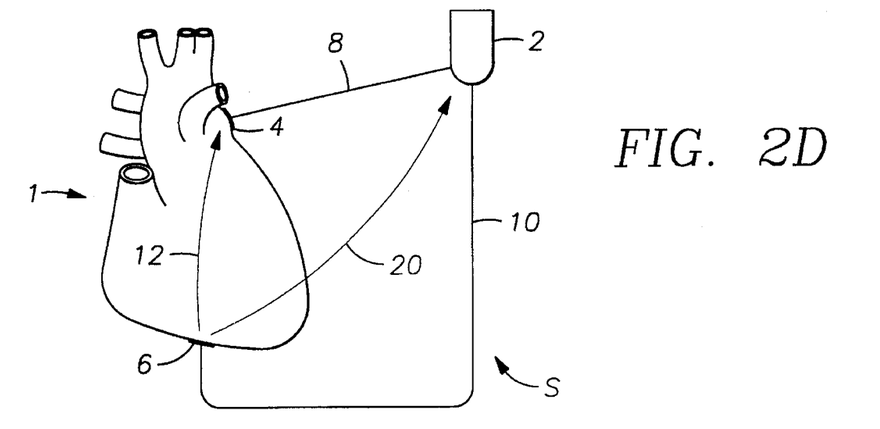

In FIG. 2A, heart 1 is assisted by an AICD system S by application of shocks capable of cardioverting or defibrillating heart inside tissue. AICD can 2 contains the circuitry and power supply for system S in a metal housing which may be used as an electrode itself, i.e. a "hot" can. Issuing from and electrically connected or connectable to can 2 are leads 8 and 10 which are, in turn, electrically connected to electrodes 4 and 6, respectively. Electrode 4 is depicted as being implanted in a superior position relative to heart 1 such as in the superior vena cava (SVC). Electrode 6 is depicted as being implanted in an inferior position in heart 1 such as in the right ventricle (RV). When a sufficient charge is developed at the high voltage capacitor of the AICD (not shown), and at a regulated interval, a shock typically comprising 600 or more volts, is electrically transferred from can 2 through lead 10 to the RV electrode 6. The current passes from RV electrode 6, into the surrounding tissue of heart 1 through the current path 12. The circuit is completed by passage of the current to SVC electrode 4 and back to can 2 via lead 8.

Where the methods and circuits of the invention are employed, it is possible in one embodiment to add an electrode if the impedance of the system rises above an acceptable impedance range. In FIG. 2D, system S is shown to have can 2 connected as an electrode. This results in the generation of an additional current path 20 by which the current arising from RV electrode 6 passes through heart 1 along both the original current path 12 and the new current path 20. Alternatively, where it is desired to remove an electrode from the system shown in FIG. 2A, it is possible to redirect the current path altogether along path 20 as shown in FIG. 2G. In this mode of operation, impedance measurement resulted in a value below the lower threshold, which in turn resulted in the disconnection of SVC electrode 4 and lead 8 while maintaining the electrical connection to the hot can electrode 2.

Figure 2E:
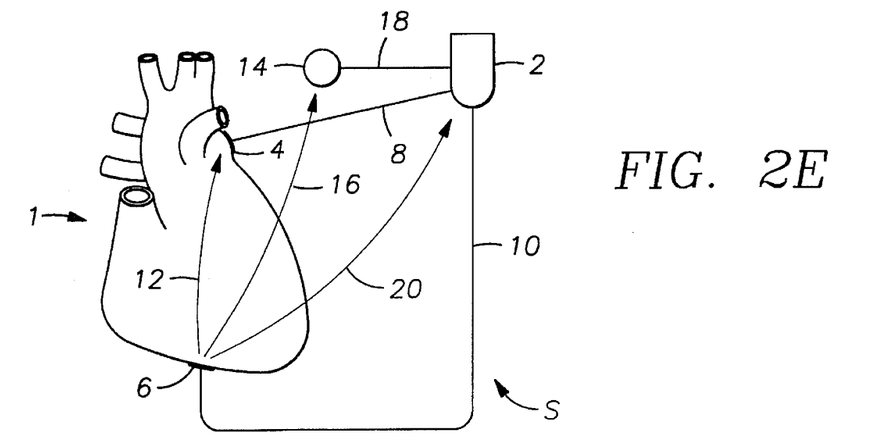
Figure 2F:
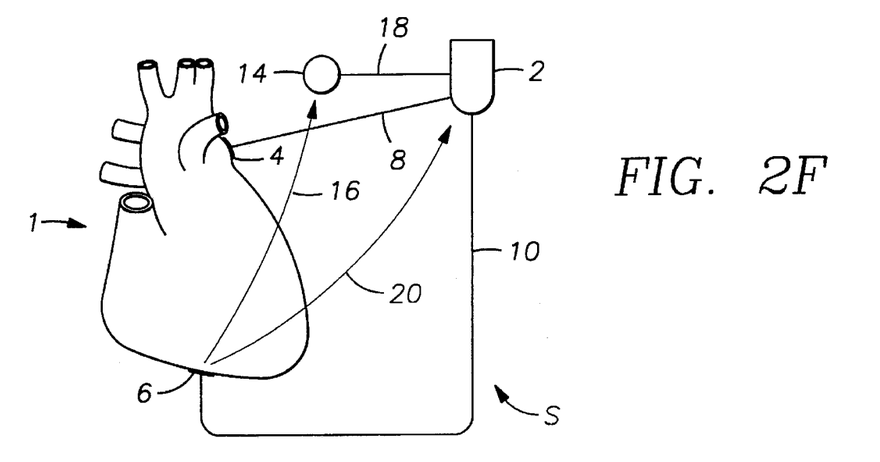
Figure 2G:
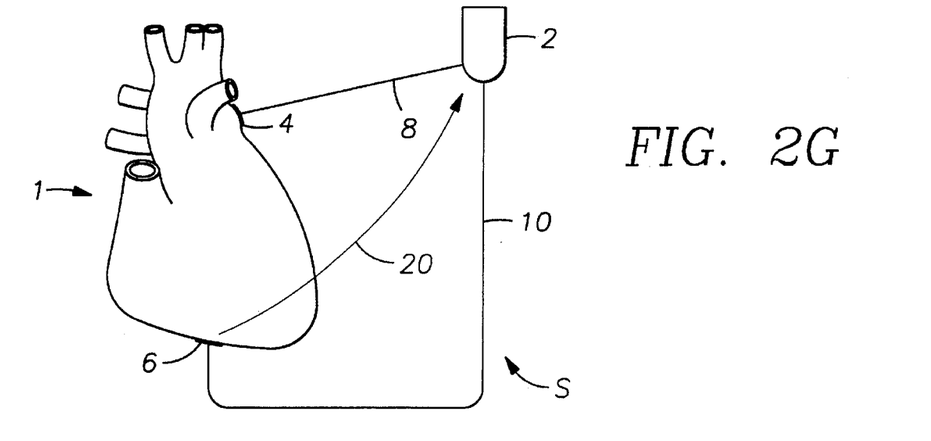
Figure 2H:
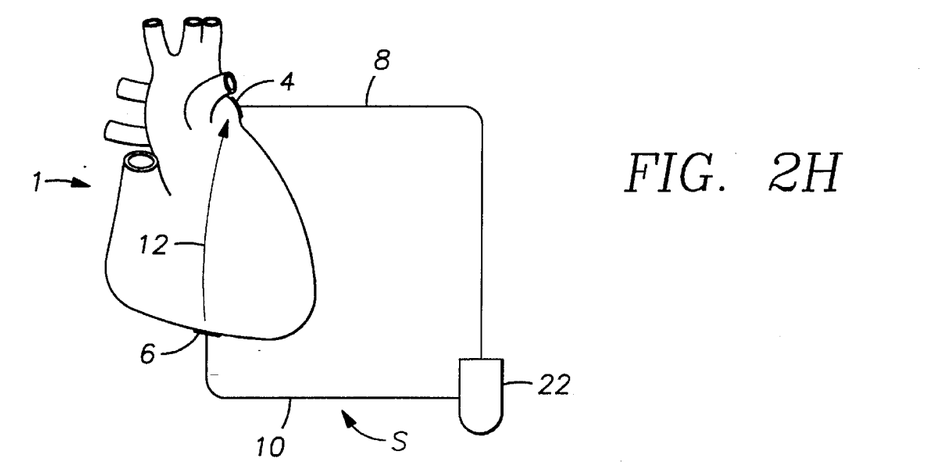
Figure 2I:
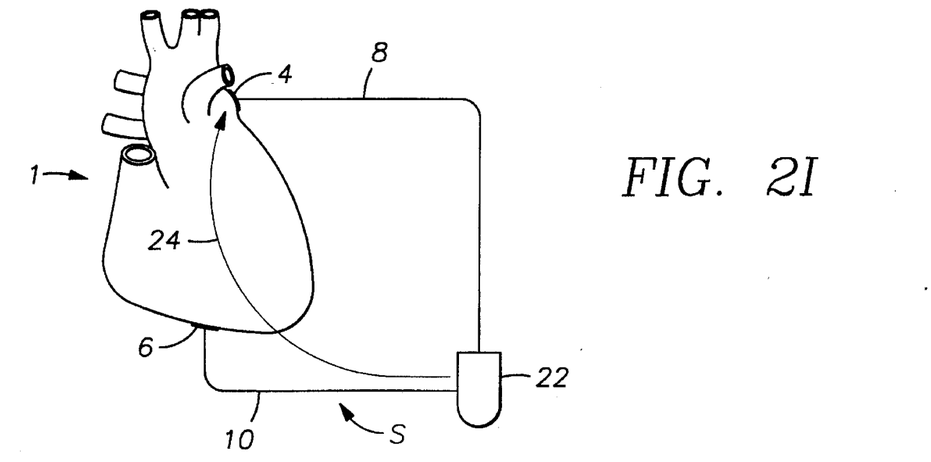

In a similar configuration, the AICD system S may have a can implanted in an abdominal position such as shown in FIGS. 2H and 2I. System S of FIG. 2H generates current path 12 in a manner consistent with that described for FIG. 2A, above. Where comparison of the measured impedance to the high impedance threshold results in a decision to add an electrode, hot can electrode 22 is connected into system S resulting in current path 24. This may result in dual current paths 12 and 24 (not shown). However, as shown in FIG. 2I, RV electrode 6 and lead 10 have been electrically disconnected from system S resulting in the single vector 24 through heart 1, as would be necessary where RV lead dislodgement of lead 10 or electrode failure of RV electrode 6 occurred.

In more complicated configurations, more alternatives exist for switching electrodes into or out of connection to the AICD system. Thus, in FIGS. 2B, C, E, and F, AICD systems are depicted with subcutaneously implanted electrode 14 in electrical connection with, or connectable through, lead 18 to can 2. Typically, such systems will initially be configured with dual current paths emanating from RV electrode 6-one vectoring to SVC electrode 4 along current path 12 and the other vectoring through heart 1 along current path 16 to subcutaneous electrode 14. Alternatively, as shown in FIG. 2C, SVC electrode 4 and lead 8 have been electrically disconnected from system S resulting in the single vector 16 from RV electrode 6 to subcutaneous electrode 14.

FIG. 2E depicts the resulting vectors (12, 16, and 20) operating simultaneously when can 2 is connected into system S which system has subcutaneous electrode 14 in addition to standard electrodes 4 and 6 implanted in or around the tissue of heart 1. When the methods and systems of the invention are used to switch off selected electrodes, the resulting vectors generate current paths such as those shown in FIG. 2F (current paths 16 and 20) and that shown in FIG. 2C (current path 16). In each instance, one or more of the electrodes which were electrically connected to system S are disconnected in order to raise the impedance above the low impedance threshold.

Figure 3:
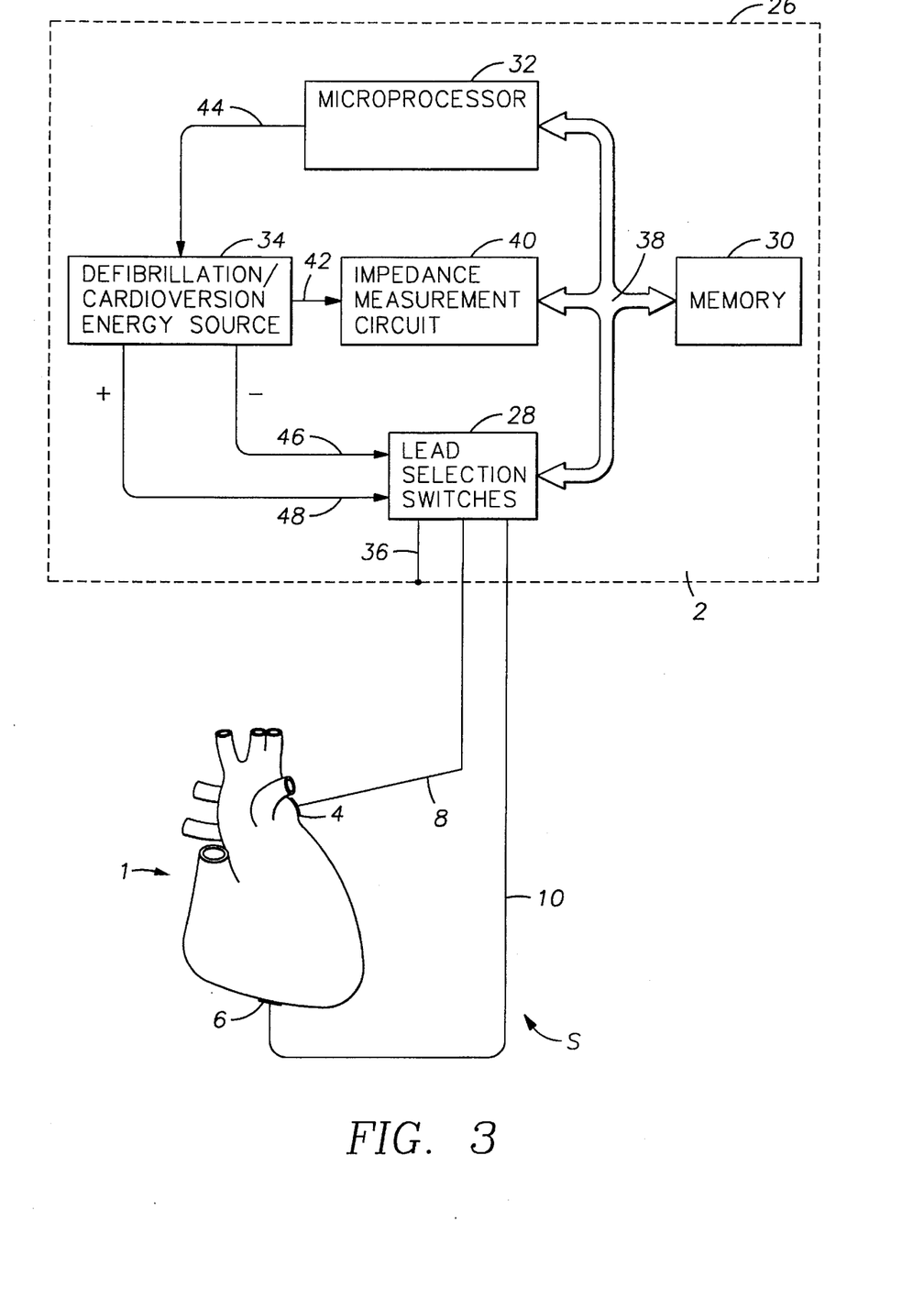
FIG. 3. Heart assisted by an AICD with electrodes which may be activated in the right ventricle, the superior vena cava, and at the can, including a block diagram of the AICD capable of switching leads.

In FIG. 3, a general block diagram of the switching circuit block is shown. FIG. 3 is analogous to FIGS. 2A, 2D and 2G (can electrode 2 disconnected, can electrode 2 connected, and SVC electrode 4 disconnected, respectively). Can 2 houses the circuitry of the AICD capable of switching among electrodes. Can 2 has a housing 26 which is electrically connected through electrical connection 36 to lead selection switches 28. Similarly, leads 8 and 10 connect respectively to SVC electrode 4 and RV electrode 10, and also are electrically connected to lead selection switches 28. The lead selection switches 28 comprise a plurality of switches which can be opened or shut, as desired, to electrically connect or disconnect electrodes 4, 6 and housing 26 to the energy source 34. Selection of switch position, either connecting or disconnecting each electrode/lead as necessary, is regulated by signals transmitted through the data bus 38. The data bus 38 interconnects lead selection switches 28 with memory 30 and microprocessor 32. Memory 30 preferably encodes predetermined high and low impedance threshold values. Microprocessor 32 includes logic to conduct the algorithmic comparison of the memorized threshold values stored in memory with the measured impedance values obtained from impedance measurement circuit 40. Microprocessor 32 also controls the AICD circuits in manners known to those of skill in the art in order to produce defibrillation/cardioversion shocks from the contained energy source 34. Polarity output terminals 46 and 48 (minus and plus, respectively) of the defibrillation/cardioversion energy source 34 are electrically connected through the lead selection switches 28 to the appropriate leads and electrodes.

Thus, for example, the configuration of FIG. 2A would require that the lead selection switches 28 be configured to connect the positive polarity output terminal 48 to RV electrode 6 through lead 10. Current applied to electrode 6 then is transmitted across vector 12 (FIG. 2A) to SVC electrode 4, and back to terminal 46 via return lead 8 to complete the circuit. Where the metal housing 26 of can 2 is connected into system S, lead switches 28 are configured by suitable signals from memory 20 and microprocessor 32 to cause housing 26 to accept current via current path 20 (FIG. 2D). This result is achieved by disconnecting electrode 4 from negative output terminal 46 of the energy source 34, and connecting lead 36 to the negative output terminal. As a result, housing 26 of can 2 functions as the ground electrode for energy source 34 by appropriate configuration of the selection switches 28. Where SVC electrode 4 and lead 8 are sensed by memory 30 and microprocessor 32 to be causing the measured impedance to drop below the low impedance threshold, lead selection switches 28 are configured to electrically disconnect lead 8 and SVC electrode 4 from the negative output terminal 46, and to connect lead 36 thereto, resulting in the current path 20 between electrode 6 and can 2 (FIG. 2G). The impedance is measured by the impedance measurement circuit 40 which monitors the defibrillation/cardioversion energy source 34 via connection 42 and communicates the measurement to the microprocessor 32 via data bus 38.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without be departing from the intended scope of the invention. For example, while the inventor has described the practice of his invention in a best mode of operation as a fully automatic, implantable system, at least certain functions carried out in fully automatic mode may be conducted in a semi-automatic or strictly manual mode. Likewise, certain of the steps may be conducted telemetrically or otherwise external to the AICD itself. Thus, for instance, where a subcutaneous electrode is used, a simple out-patient operation may be conducted to connect or disconnect that electrode from the system. Similarly, while the invention described is designed to make one or a few connect/disconnect operations, fully dynamic systems capable of constantly assessing and modifying the electrode configuration necessary for long-term cardioversion/defibrillation management are possible. All such modifications are intended to be included within the scope of the appended claims.

What is claimed is:

1. A method of maximizing likelihood of successful defibrillation or cardioversion of a heart using an automatic implantable cardioverter/defibrillator system, comprising:

measuring the shock electrode impedance of said system between at least two electrodes;

comparing said impedance to a high impedance threshold;

where said impedance is approximately above said high impedance threshold, connecting at least one additional electrode to said system; and, creating at least one shocking current vector which passes through a mass of cardiac tissue sufficient to cardiovert/defibrillate said heart.

2. A method of maximizing likelihood of successful defibrillation or cardioversion of a heart using an automatic implantable cardioverter/defibrillator system, comprising:

measuring the shock electrode impedance of said system between at least three electrodes;

comparing said impedance to a low impedance threshold;

where said impedance is approximately below said low impedance threshold, disconnecting at least one of said electrodes from said system; and, creating at least one shocking current vector which passes through a mass of cardiac tissue sufficient to cardiovert/defibrillate said heart.

3. A method of maximizing likelihood of successful defibrillation or cardioversion of a heart using an automatic implantable cardioverter/defibrillator system, comprising:

measuring the shock electrode impedance of said system between at least two electrodes;

comparing said impedance measurement to a high impedance threshold;

where said impedance measurement is approximately above said high impedance threshold, connecting at least one additional electrode to said system, and;

comparing said impedance measurement to a low impedance threshold;

where said impedance measurement is approximately below said low impedance threshold, disconnecting at least one electrode from said system; and creating at least one shocking current vector which passes through a mass of cardiac tissue sufficient to cardiovert/defibrillate said heart.

4. The method of claim 3 wherein impedance approximately above or below said thresholds is a result of lead dislodgement.

5. The method of claim 3 wherein impedance above or below said thresholds is a result of lead malfunction.

6. The method of claim 3 wherein impedance above or below said thresholds is a result of acute phase tissue stabilization after implantation.

7. The method of claim 3 wherein said electrode is an electrode implanted in or near a superior vena cava.

8. The method of claim 3 wherein said electrode is an electrode implanted in or near a right ventricle.

9. The method of claim 3 wherein said electrode is an electrode implanted subcutaneously.

10. The method of claim 3 wherein said electrode is an electrode implanted in or near a coronary sinus.

11. The method of claim 3 wherein said electrode is an implantable cardioverter/defibrillator can.

12. The method of claim 11 wherein said can is implanted pectorally.

13. The method of claim 11 wherein said electrode is implanted abdominally.

14. The method of claim 3 wherein said impedance is calculated using the formula:

$$R = \frac{t}{C \ln\left(\frac{V_i}{V_f}\right)}$$

wherein R=impedance; T=duration of delivered shock; $V_i$=pre-shock voltage reading; $V_f$=post-shock voltage reading; and C=capacitance.

15. The method of claim 3 wherein said impedance is measured at a capacitor prior to shock and following shock.

16. The method of claim 3 wherein said high impedance threshold is between approximately 50 and 100 Ohms.

17. The method of claim 3 wherein said high impedance threshold is between approximately 60 and 80 Ohms.

18. The method of claim 3 wherein said high impedance threshold is approximately 70 Ohms.

19. The method of claim 3 wherein said low impedance threshold is between approximately 20 and 60 Ohms.

20. The method of claim 3 wherein said low impedance threshold is between approximately 30 and 40 Ohms.

21. The method of claim 3 wherein said low impedance threshold is approximately 40 Ohms.

22. The method of claim 3 wherein said system comprises a hot can electrode, a superior vena cava implanted electrode, and a right ventricle implanted electrode.

23. The method of claim 3 wherein said system comprises a hot can electrode, a superior vena cava implanted electrode, a right ventricle implanted electrode, and a subcutaneously implanted electrode.

24. The method of claim 3 wherein said system comprises a hot can electrode, a right ventricle implanted electrode, and a subcutaneously implanted electrode.

25. A system for maximizing likelihood of successful defibrillation or cardioversion of a heart using an automatic implantable cardioverter/defibrillator system, comprising:

an impedance measurement device for measuring the shock electrode impedance of said system between at least two electrodes;

an comparator for comparing said impedance to a high impedance threshold value; and, a plurality of switches for connecting at least one additional electrode to said system, when said impedance rises above said high impedance threshold, said system capable of creating at least one shocking current vector which passes through a mass of cardiac tissue sufficient to cardiovert/defibrillate said heart.

26. A system for maximizing likelihood of successful defibrillation or cardioversion of a heart using an automatic implantable cardioverter/defibrillator system, comprising:

an impedance measurement device for measuring the shock electrode impedance of said system between at least three electrodes;

a comparator for comparing said impedance to a low impedance threshold value; and, a plurality of switches for disconnecting at least one of said electrodes from said system, when said impedance is approximately below said low impedance threshold, said system capable of creating at least one shocking current vector which passes through a mass of cardiac tissue sufficient to cardiovert/defibrillate said heart.

27. A system for maximizing likelihood of successful defibrillation or cardioversion using an automatic implantable cardioverter/defibrillator system, comprising:

an impedance measurement device for measuring the shock electrode impedance of said system between at least two electrodes;

a comparator for comparing said impedance measurements to a high impedance threshold value;

a plurality of switches for electrically connecting at least one additional electrode to said system when said impedance measurements are approximately above said high impedance threshold;

a comparator for comparing said impedance measurements to a low impedance threshold value; and, a plurality of switches for electrically disconnecting at least one of said electrodes from said system when said impedance measurements are approximately below said low impedance threshold, said system capable of creating at least one shocking current vector which passes through a mass of cardiac tissue sufficient to cardiovert/defibrillate said heart.

* * * * *